United States Patent [19]

Thomas et al.

[11] Patent Number: 5,294,716
[45] Date of Patent: Mar. 15, 1994

[54] CHEMICAL PROCESS FOR MAKING ANGIOTESIN II ANTAGONIST COMPOUNDS

[75] Inventors: Andrew P. Thomas, Congleton; David M. G. Martin, Stockport; Stanley A. Lee; Lyn Powell, both of Macclesfield, all of England

[73] Assignee: Imperial Chemical Industries PLC, London, England

[21] Appl. No.: 822,395

[22] Filed: Jan. 17, 1992

[30] Foreign Application Priority Data

Jan. 17, 1991 [GB] United Kingdom ............... 9101026
Apr. 2, 1991 [GB] United Kingdom ............... 9106876
Oct. 14, 1991 [GB] United Kingdom ............... 9121726

[51] Int. Cl.$^5$ .................. C07D 257/06; C07D 401/08
[52] U.S. Cl. .................................. 546/135; 546/276; 548/250; 548/252; 548/253; 548/254
[58] Field of Search ............. 546/276, 135; 548/250, 548/252, 253, 254

[56] References Cited

FOREIGN PATENT DOCUMENTS 253310 1/1988 European Pat. Off. .
291969 11/1988 European Pat. Off. .
412848 2/1991 European Pat. Off. .
453210 10/1991 European Pat. Off. .

OTHER PUBLICATIONS

G. Bianchetti et al. "Distacco per idrazinolisi del gruppo 2,4-dinitrofenilico.-Nota II. Idrazinolisi di 1-(2-,4-dinitro)fenil-v-triazoli e-tetrazoli." *Gazz. Chim. Ital.* (1968), 94, 340-355. (Summary in English).

K. Kamala, et al., *Bull. Chem. Soc. JPN.* (1988) 61, No. 10, 3791-3793; "Synthesis of 2-Aryl[1,2,4]triazolo[1,5-a pyrimidines".

P. G. Houghton, et al., *J. Chem. Soc. Perkin Trans I* (1985), 1471-1479: "Intramolecular Reaction Between Nitro and Carbodi-imide Groups; A New Synthesis of 2-Arylbenzotriazoles".

*Primary Examiner*—C. Warren Ivy
*Assistant Examiner*—Phyllis G. Spivack
*Attorney, Agent, or Firm*—Thomas F. Jackson

[57] ABSTRACT

The invention provides a novel chemical process for the manufacture of quinoline, pyridine and imidazole derivatives of the formula IV wherein Q, $Y^1$ and $Y^2$ have the various meanings defined herein, and their non-toxic salts, which are angiotensin II inhibitors. The process involves the removal of an electron-deficient phenyl group or a pyridyl or pyrimidyl group from a compound of the formula VI as defined herein.

9 Claims, No Drawings

CHEMICAL PROCESS FOR MAKING ANGIOTESIN II ANTAGONIST COMPOUNDS

This invention concerns a novel chemical process for the production of certain quinoline, pyridine and imidazole derivatives, which derivatives possess pharmacologically useful properties in antagonising at least in part one or more of the actions of substances known as angiotensins, and in particular of that known as angiotensin II (hereinafter referred to as "AII"). The invention also concerns various quinoline, pyridine and imidazole derivatives which are valuable chemical intermediates, for example for use in the abovementioned process.

The angiotensins are key mediators of the renin-angiotensinaldosterone system, which is involved in the control of homeostasis and fluid/electrolyte balance in many warm-blooded animals, including man. The angiotensin known as AII is produced by the action of angiotensin converting enzyme (ACE) from angiotensin I, itself produced by the action of the enzyme renin from the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. AII inhibitors are useful for the reduction or prevention of these effects produced by the action of AII. Although a number of AII inhibitors are known, there remains a continuing need for alternative inhibitors and for effective synthetic procedures for the production of both new and known AII inhibitors such as that provided by this invention.

In our co-pending European Patent Application, Publication No. 412848, there is described a series of quinoline derivatives (possessing AII antagonist properties) of formula I (set out hereinafter) wherein $R^1$ is hydrogen, (1–8C)alkyl, (3–8C)cycloalkyl, phenyl or substituted (1–4C)alkyl, the latter containing one or more fluoro substituents or bearing a (3–8C)cycloalkyl, hydroxy, (1–4C)alkoxy or phenyl substituent; $R^2$ is hydrogen, (1–8C)alkyl, (3–8C)cycloalkyl, (3–8C)cycloalkyl-(1–4C)alkyl, carboxy, (1–4C)alkoxycarbonyl, cyano, nitro, phenyl or phenyl(1–4C)alkyl; $R^3$ and $R^4$ are independently selected from hydrogen, (1–4C)alkyl, (1–4C)alkoxy, fluoro(1–4C)alkoxy, halogeno, hydroxy, trifluoromethyl, cyano, nitro, amino, (1–4C)alkanoylamino, alkylamino and dialkylamino of up to 6 carbon atoms, dialkylamino-alkyl of 3 to 8 carbon atoms, (1–4C)alkanoyl, carbamoyl, $\underline{N}$-alkylcarbamoyl and di-($\underline{N}$-alkyl)carbamoyl of up to 7 carbon atoms, carboxy, (1–4C)alkoxycarbonyl, (1–6C)alkylthio, (1–6C)alkylsulphinyl, (1–6C)alkylsulphonyl, and substituted (1–4C)alkyl, the latter bearing an amino, hydroxy or (1–4C)alkoxy substituent; or $R^3$ and $R^4$ together form (1–4C)alkylenedioxy attached to adjacent carbon atoms of the benzene moiety of formula I; Ra and $R^5$ are independently selected from hydrogen, (1–4C)alkyl, (1–4C)alkoxy, halogeno, trifluoromethyl, cyano or nitro; A is methylene; X is phenylene optionally bearing a substituent selected from (1–4C)alkyl, (1–4C)alkoxy, halogeno, trifluoromethyl, cyano and nitro, or X is a direct bond between the adjacent phenyl group and moiety A; Za is 1H-tetrazol-5-yl, —CO.NH.(1H-tetrazol-5-yl) or a group of the formula —CO.OR$^6$ or —CO.NH.SO$_2$.R$^7$ in which $R^6$ is hydrogen or a non-toxic, biodegradable residue of a physiologically acceptable alcohol or phenol, and $R^7$ is (1–6C)alkyl, (3–8C)cycloalkyl or phenyl; and wherein any of said phenyl moieties may be unsubstituted or bear one or two substituents independently selected from (1–4C)alkyl, (1–4C)alkoxy, halogeno, cyano and trifluoromethyl; or a non-toxic salt thereof; but excluding methyl 2-[(3-methoxycarbonylquinolin-4-yloxy)methyl]benzoate.

A specific value for X which is of particular interest is, for example, p-phenylene.

A preferred value for $R^5$ is, for example, hydrogen and for $R^1$ is, for example, methyl, ethyl or propyl.

An especially preferred value for Za is, for example, 1H-tetrazol-5-yl and, in particular, when it is attached ortho to the group X.

Compounds disclosed in said co-pending application which are particularly preferred include 2-methyl-4-[(2'-(1H-tetrazol-5-yl)biphenyl-4-yl)methoxy]quinoline, 2-ethyl-4-[(2'-(1H-tetrazol-5-yl)biphenyl-4-yl)methoxy]quinoline, 2-ethyl-7-hydroxymethyl-4-[(2'-(1H-tetrazol-5-yl)biphenyl-4-yl)methoxy]quinoline, 2-ethyl-6-(2-fluoroethoxy)-4-[(2'-(1H-tetrazol-5-yl)biphenyl-4-yl)methoxy]quinoline, 2-ethyl-6-(2,2,2-trifluoroethoxy)-4-[(2'-(1H-tetrazol-5-yl)biphenyl-4-yl)methoxy]quinoline and 2-ethyl-6-isopropoxy-4-[(2'-(1H-tetrazol-5-yl)biphenyl-4-yl)methoxy]quinoline, together with their non-toxic salts.

We are also aware, for example as described in our separate co-pending European patent application, publication no. 453210, of a series of pyridine derivatives (possessing AII antagonist properties) of formula II (set out hereinafter) wherein $T^1$ is hydrogen, (1–8C)alkyl, (3–8C)cycloalkyl, phenyl or substituted (1–4C)alkyl, the latter containing one or more fluoro substituents or bearing a (3–8C)cycloalkyl, (1–4C)alkoxy or phenyl substituent; $T^2$ is hydrogen, (1–8C)alkyl, (3–8C)cycloalkyl, (3–8C)cycloalkyl-(1–4C)alkyl, carboxy, (1–4C)alkoxycarbonyl, (3–6C)alkenyloxycarbonyl, cyano, nitro, phenyl or phenyl(1–4C)alkyl; $T^3$ is selected from halogeno, (1–4C)alkoxy, amino, alkylamino and dialkylamino of up to 6 carbon atoms, and any of the values defined for $T^1$; $T^4$ is selected from hydrogen, (1–4C)alkyl optionally bearing an amino, (1–4C)alkanoylamino, phenylcarbonylamino, hydroxy or (1–4C)alkoxy substituent, carboxy, (1–4C)alkoxycarbonyl, (3–6C)alkenyloxycarbonyl, cyano, nitro, carbamoyl, (1–4C)alkanoyl, $\underline{N}$-alkylcarbamoyl and di-($\underline{N}$-alkyl)carbamoyl of up to 7 carbon atoms, formyl, halogeno, amino, alkylamino and dialkylamino of up to 6 carbon atoms, 3-(1–4C)alkylureido and (1–4C)alkanoylamino; or $T^4$ is a group of the formula —A$^1$.A$^2$.E wherein A$^1$ is carbonyloxy, A$^2$ is (1–6C)alkylene and E is selected from hydroxy, (1–4C)alkoxy, phenyloxy, phenyl(1–4C)alkoxy, pyridyl(1–4C)alkoxy, 4-morpholino(1–4C)alkoxy, phenylamino, amino, alkylamino and dialkylamino of up to 6 carbon atoms, (1–4C)alkanoylamino, (1–4C)alkylsulphonylamino, phenylsulphonylamino, sulphamoylamino (—NH.SO$_2$.NH$_2$), carboxamidomethylamino (—NH.CH$_2$.CO.NH$_2$), (1–4C)alkanoyloxy, phenylcarbonyloxy, aminocarbonyloxy (—O.-CO.NH$_2$), (1–4C)alkylaminocarbonyloxy, carboxy, (1–4C)alkoxycarbonyl, carbamoyl, $\underline{N}$-alkylcarbamoyl and di-($\underline{N}$-alkyl)carbamoyl of up to 7 carbon atoms, (1–4C)alkanoyl, 4-morpholino, 1-imidazolyl and succinimido group; or E is a group of the formula —A$^3$.E$^1$ wherein A$^3$ is oxy, oxycarbonyl or imino and E$^1$ is a 5 or 6-membered saturated or unsaturated heterocyclic ring containing 1 or 2 nitrogen atoms and linked to A$^3$ by a ring carbon atom; or $A^3$ is oxycarbonyl and $E^1$ is a 4-morpholino group or a 5 or 6-membered saturated heterocyclic ring containing 1 or 2 nitrogen atoms, optionally bearing a (1–4C)alkyl group and linked to $A^3$ by a ring nitrogen atom; and wherein $E^1$ the remainder of the ring atoms are carbon; or $T^3$ and $T^4$ together form (3–6C)alkylene, one of the methylene groups of which may optionally be replaced by a carbonyl group, or (3–6C)alkenylene; $T^5$ is hydrogen; $T^6$ is hydrogen or (1–4C)alkyl; $T^7$ is selected from hydrogen, (1–4C)alkyl, (1–4C)alkoxy, halogeno, trifluoromethyl, cyano and nitro; U is phenylene optionally bearing a substituent selected from (1–4C)alkyl, (1–4C)alkoxy, halogeno, (1–4C)alkanoyl, trifluoromethyl, cyano and nitro, or U is a direct bond between the adjacent phenyl group and the carbon atom bearing $T^5$ and $T^6$; Zb is 1H-tetrazol-5-yl, —CO.NH.(1H-tetrazol-5-yl) or a group of the formula —CO.O$T^8$ or —CO.NH.SO$_2$.$T^9$ in which $T^8$ is hydrogen or a non-toxic, biodegradable residue of a physiologically acceptable alcohol or phenol, and $T^9$ is (1–6C)alkyl, (3–8C)cycloalkyl or phenyl; and wherein any of said phenyl moieties may be unsubstituted or bear one or two substituents independently selected from (1–4C)alkyl, (1–4C)alkoxy, halogeno, cyano and trifluoromethyl; or an N-oxide thereof; or a non-toxic salt thereof.

A specific value for U which is of particular interest is, for example, p-phenylene.

A preferred value for $T^1$ or $T^3$ is, for example, methyl or ethyl.

A preferred value for $T^2$ is, for example, hydrogen, unsubstituted phenyl or phenyl bearing one or two substituents independently selected from methyl, ethyl, methoxy, ethoxy, fluoro, chloro, bromo, iodo, cyano and trifluoromethyl.

A preferred value for $T^4$ is, for example, hydrogen, alkoxycarbonyl or alkenyloxycarbonyl.

A preferred value for $T^6$ is, for example, hydrogen.

A preferred value for $T^3$ and $T^4$ when together they form alkylene is, for example, trimethylene or tetramethylene.

A preferred value for Zb is, for example, 1H-tetrazol-5-yl and which is especially preferred when attached ortho to the group U.

A particularly preferred combination of values is, for example, when $T^1$ and $T^3$ are both alkyl, or when $T^1$ is alkyl and $T^3$ together with $T^4$ form alkylene.

Compounds disclosed in our said co-pending applications which are of special interest are: methyl 2,6-dimethyl-4-[(2'-(1H-tetrazol-5-yl)biphenyl-4-yl)methoxy]pyridine-3-carboxylate; 2-ethyl-5,6,7,8-tetrahydro-4-[(2'-(1H-tetrazol-5-yl)biphenyl-4-yl)methoxy]quinoline; 6,7-dihydro-2-methyl-4-[(2'-(1H-tetrazol-5-yl)biphenyl-4-yl)methoxy]-5H-cyclopenta[b]pyridine; methyl 2-ethyl-6-methyl-4-[(2'-(1H-tetrazol-5-yl)biphenyl-4-yl)methoxy]pyridine-3-carboxylate; methyl 6-ethyl-2-methyl-4-[(2'-(1H-tetrazol-5-yl)biphenyl-4-yl)methoxy]pyridine-3-carboxylate; methyl 2,6-diethyl-4-[(2'-(1H-tetrazol-5-yl)biphenyl-4-yl)methoxy]pyridine-3-carboxylate; 6,7-dihydro-2-ethyl-4-[(2'-(1H-tetrazol-5-yl)biphenyl-4-yl)methoxy-5H-cyclopenta[b]pyridine; 2,6-dimethyl-3-phenyl-4-[(2'-(1H-tetrazol-5-yl)biphenyl-4-yl)methoxy]pyridine; and allyl 2,6-dimethyl-4-[(2'-(1H-tetrazol-5-yl)biphenyl-4-yl)methoxy]pyridine-3-carboxylate; and the non-toxic salts thereof.

In the above-mentioned published European patent applications, the compounds of the formula I and II defined therein include racemic and optically active forms which possess the useful pharmacological properties described therein where one or more chiral centres are present. In addition generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

In European Patent Application, Publication No. 253310 there are described imidazole derivatives of the formula III (set out hereinafter) wherein Alk. is a (3–10-C)alkyl group, $X^1$ is selected from hydrogen, fluoro, chloro, bromo, iodo, nitro, trifluoromethyl and cyano; and $L^1$ and $L^2$ are selected from hydrogen, fluoro, chloro, bromo, iodo, nitro, (1–4C)alkyl and (1–4C)alkoxy. These compounds are described therein as possessing AII antagonist properties.

We have now discovered a simple alternative procedure for the production of certain quinoline derivatives of the formula I or pyridine derivatives of the formula II wherein X and U are optionally substituted p-phenylene and Za and Zb are tetrazolyl, or imidazole derivatives of the formula III, wherein the other variables have any of the values defined hereinbefore.

According to the invention there is provided a process for the manufacture of a compound of formula IV (set out hereinafter), wherein Q is selected from a 4-quinolyloxy moiety of the formula Va (set out hereinafter) wherein $R^1$, $R^2$, $R^3$, $R^4$ and Ra have any of the meanings defined hereinbefore, a 4-pyridyloxy moiety of the formula Vb (set out hereinafter) wherein $T^1$, $T^2$, $T^3$ and $T^4$ have any of the meanings defined hereinbefore and a 1-imidazolyl moiety of the formula Vc (set out hereinafter) wherein Alk. and $X^1$ have any of the meanings defined hereinbefore; $Y^1$ is selected from hydrogen, (1–4C)alkyl, (1–4C)alkoxy, halogeno, (1–4C)alkanoyl, trifluoromethyl, cyano and nitro; and $Y^2$ is selected from hydrogen, (1–4C)alkyl, (1–4C)alkoxy, halogeno, trifluoromethyl, cyano and nitro; which comprises reaction of a compound of the formula VI wherein $P^1$ is an electron-deficient phenyl group or is a pyridyl or pyrimidyl group, and Q, $Y^1$ and $Y^2$ have any of the meanings defined above, with a base selected from an alkali metal hydroxide, (1–12C)alkanolate, (1–12C)alkanethiolate, phenolate, thiophenolate and diphenylphosphide, wherein any phenyl ring of the latter three groups may optionally bear a (1–4C)alkyl, (1–4C)alkoxy or halogeno substituent.

A particular value for $P^1$ when it is an electron-deficient phenyl group includes, for example, a phenyl group bearing 1, 2 or 3 electron-withdrawing groups independently selected from halogeno (typically chloro or bromo), nitro, cyano, trifluoromethyl, di(1–4C)alkylaminosulphonyl (such as dimethylaminosulphonyl or diethylaminosulphonyl) and (1–4C)alkylsulphonyl (such as methylsulphonyl or ethylsulphonyl).

Suitable bases are, by way of example: for an alkali metal hydroxide: sodium or potassium hydroxide; for an alkali metal alkanolate: an alkali metal (1–8C)alkanolate, for example an alkali metal (1–4C)alkoxide, such as sodium or potassium methoxide, ethoxide, propoxide or butoxide; for an alkali metal alkanethiolate: an alkali metal (1–8C)alkanethiolate, for example an alkali metal (1–4C)alkanethiolate such as sodium or potassium methanethiolate, ethanethiolate, propanethiolate or butanethiolate; for a phenolate or thiophenolate: the sodium or potassium salt of phenol, thiophenol, or a phenol or thiophenol bearing a methyl, ethyl, methoxy, ethoxy, fluoro, chloro, bromo or iodo group.

A particular value for $Y^1$, $Y^2$ or for an optional substituent on a phenyl group of an alkali metal phenolate, thiophenolate or diphenylphosphide, when it is alkyl is, for example, methyl or ethyl; when it is alkoxy is, for example, methoxy or ethoxy; and when it is halogeno is, for example, fluoro, chloro or bromo.

A particular value for $Y^1$ when it is alkanoyl is, for example, formyl, acetyl or propionyl.

A preferred value for $P^1$ is, for example, a nitrophenyl group or a 4-pyridyl, 4-cyanophenyl, 4-dimethylaminosulphonyl, 4-methylsulphonyl or 3-cyano-4-trifluoromethylphenyl group. Of these 4-nitrophenyl is especially preferred.

A preferred value for $Y^1$ or $Y^2$ is, for example, hydrogen, an especially preferred combination being when $Y^1$ and $Y^2$ are both hydrogen.

A particularly preferred base is an alkali metal alkanethiolate such as sodium or potassium propanethiolate, an alkali metal alkanolate such as sodium or potassium methoxide or ethoxide, or an alkali metal thiophenolate such as sodium or potassium 4-fluorothiophenolate.

It will be appreciated that when the base is an alkali metal alkanolate, alkanethiolate, phenolate, thiophenolate or diphenylphosphide, it may be generated in situ from the corresponding alkanol, alkanethiol, phenol, thiophenol or diphenylphosphine with a suitable alkali metal base such as an alkali metal hydride, for example, lithium, potassium or sodium hydride. Alternatively when an alkali metal alkanolate is used, it may be convenient to employ the base as a solution in the corresponding alcohol (for example a solution of sodium methoxide in methanol).

The process of the invention is particularly useful for the preparation of compounds of the formula IV wherein the tetrazolyl group is at the ortho position relative to the adjacent phenyl group.

The process of the invention is also particularly useful for the preparation of compounds of the formula IV wherein Q is a 4-quinolyloxy of the formula Va or 4-pyridyloxy group of the formula Vb as defined above, and especially when the tetrazole group is at the ortho position relative to the adjacent phenyl group. Particular values for $R^1$, $R^2$, $R^3$ and $R^4$ in Q when it is a 4-quinolyloxy moiety of formula Va are, for example, those particular and preferred values, and preferred combinations thereof, which are given in co-pending EPA 412848, for example a particular value for $R^1$ is methyl, ethyl or propyl. Particular values for $T^1$, $T^2$, $T^3$ or $T^4$ in Q when it is a 4-pyridyloxy moiety of formula Vb are, for example, those particular and preferred values, and preferred combinations thereof, which are given in co-pending EPA 453210. In particular, the process is especially useful for the preparation of those compounds described in our co-pending applications as being particularly preferred or of special interest. Specific embodiments of the invention which are of special interest include, for example, those set out hereinafter in the accompanying Examples.

The reaction is conveniently carried out in a suitable inert organic solvent or diluent, for example, a polar solvent such as N,N-dimethylformamide or N-methylpyrrolidone. Alternatively, or in admixture, an alkanol such as methanol or ethanol may be used, for example, when an alkali metal hydroxide or alkoxide such as sodium or potassium hydroxide, methoxide or ethoxide is employed. The reaction is generally carried out at a temperature in the range, for example, −30° C. to 50° C. It will be appreciated that the choice of temperature will depend on the nature of the base employed. For example, when an alkali metal alkanethiolate or alkanolate is used, a temperature in the range of 0° C. to ambient temperature is preferred.

Compounds of the formula VI as defined hereinbefore may be obtained, for example, by alkylation of a compound of the formula VIIIa wherein $R^1$ is other than hydrogen, a compound of the formula VIIIb wherein $T^1$ and $T^3$ are other than hydrogen, or a compound of the formula VIIIc, wherein the other variables have any of the meanings defined hereinbefore, with a compound of the formula VIIa wherein $P^1$, $Y^1$ and $Y^2$ have any of the meanings defined hereinbefore and Hal. stands for a suitable leaving group such as chloro, bromo, iodo, methanesulphonyloxy or p-toluenesulphonyloxy.

The alkylation is generally carried out in the presence of a suitable base, for example, an alkali metal alkoxide such as sodium methoxide or sodium ethoxide, an alkali metal carbonate such as sodium carbonate or potassium carbonate, or an alkali metal hydride such as sodium hydride or an organic base such as diisopropylethylamine and in a solvent or diluent, for example, a (1–4C-)alkanol such as methanol or ethanol when an alkali metal alkoxide is used, or in a polar solvent such as N,N-dimethylformamide or N-methylpyrrolidone and at a temperature in the range, for example, 10°–100° C. Alternatively, a quaternary ammonium hydroxide may be used in a mixture of an aqueous or non-aqueous solvent such as water and dichloromethane.

Compounds of the formula VI wherein Q is a 4-quinolyloxy moiety of the formula Va or a 4-pyridyloxy moiety of the formula Vb may also be obtained, for example, by reaction of an alcohol of the formula VIIb with a compound of the formula Xa or Xb wherein $P^2$ is a suitable leaving group (such as chloro, bromo, iodo, methanesulphonyloxy, p-toluenesulphonyloxy or trifluoromethanesulphonyloxy). The reaction is generally carried out in the presence of a suitable base, for example an alkali metal alkoxide such as sodium methoxide or ethoxide or an alkali metal hydride such as sodium hydride and in a suitable solvent or diluent, for example a (1–4C)alkanol such as methanol or ethanol when an alkali metal alkoxide is used, or a polar solvent such as N,N-dimethylformamide. Alternatively, an alcohol of the formula VIIb may be used in the form of its preformed alkali metal salt. The reaction is usually performed at a temperature in the range of 40° to 120° C.

The compounds of the formula Xa and Xb may be obtained, for example, by halogenation of the corresponding compound of formula VIIIa and VIIIb respectively, for example, by reaction with phosphorus oxychloride in the absence of a solvent, or in the presence of an inert solvent or diluent such as toluene or dioxane, and at a temperature in the range 60°–110° C. Compounds of the formula Xa or Xb wherein $P^2$ is methanesulphonyloxy, p-toluenesulphonyloxy or trifluoromethanesulphonyloxy and $R^1$, $T^1$ and $T^3$ are other than hydrogen may be obtained, for example, by acylation of the corresponding compounds of formula VIIIa or VIIIb with the corresponding sulphonyl chloride under standard conditions. Compounds of the formula Xa or Xb wherein $P^2$ is methanesulphonyl may be obtained from alkylation of the corresponding mercaptoquinolines or mercaptopyridines followed by oxidation under standard conditions.

Certain compounds of the formula VIIIa, VIIIb and VIIIc are already known and others may be obtained by analogy therewith using standard procedures of organic chemistry well known in the art, for example as described in standard works of heterocyclic chemistry such as that edited by Elderfield, or in Org. Syn. 1951., Coll. Vol. III, pages 374 and 593; *Monatshefte fur Chemie,*. 1969, 100, 132; *J. Chem. Soc.* (B), 1968, 866; *Liebigs. Ann. Chem.*, 1982, 1656; *Heterocycles*, 1982, 13, 239; or in European Patent Applications, Publication Nos. 412848, 453210 and 253310. The compounds of the formula VIIa and VIIb may be obtained from compounds of the formula IXa, for example, as illustrated in Scheme 1 for compounds in which the tetrazole group is ortho to the adjacent phenyl ring. Thus, for example, 5-(4'-bromomethylbiphenyl-2-yl)-1-(4-nitrophenyl)-1H-tetrazole may be converted into 5-(4'-hydroxymethylbiphenyl-2-yl)-1-(4-nitrophenyl)-1H-tetrazole (using for example the procedure of Scheme 1, step (e)) which itself can be converted, for example, to 5-(4'-mesyloxymethylbiphenyl-2-yl)-(4-nitrophenyl)-1H-tetrazole or 5-(4'-tosyloxymethylbiphenyl-2-yl)-(4-nitrophenyl)-1H-tetrazole by reaction with methanesulphonyl chloride or p-toluenesulphonyl chloride respectively under standard conditions.

Alternatively, compounds of the formula VI may be obtained by reaction of a boronic acid of the formula XIa, XIb or XIc wherein the variables have any of the meanings defined hereinbefore with a compound of the formula IX wherein $P^1$ has any of the meanings defined hereinbefore and W is a bromo, iodo or trifluoromethanesulphonyloxy group, in the presence of a palladium(0) catalyst (such as tetrakis(triphenylphosphine)palladium) or a palladium(II) catalyst (such as palladium-(II) chloride), and optionally in the presence of azo(-bisisobutyronitrile). The reaction is preferably carried out in the presence of a base, such as sodium or potassium carbonate, in an inert solvent or diluent, for example, a hydrocarbon such as toluene or xylene, an ether, such as dioxan or tetrahydrofuran, an (1–4C)alkanol such as methanol or ethanol, water, or mixture thereof, for example a mixture of water, methanol and toluene, and at a temperature in the range of, for example, 50° C. to 150° C., and conveniently at or about the reflux temperature of the solvent or mixture of solvents used.

Compounds of the formula XIa, XIb or XIc may be obtained, for example, by heating at reflux a 4-methylphenylboronic acid in a solvent such as methyl chloroform with azeotropic removal of water, followed by radical bromination of the product which may be carried out in situ, for example with bromine and azo(-bisisobutyronitrile). The resultant 4-bromomethylphenylboronic acid anhydride may then be used to alkylate a compound of the formula VIIIa, VIIIb or VIIIc using similar alkylation conditions to those described above, followed by subsequent acidic hydrolysis, to give a formula XIa, XIb or XIc compound. Alternatively the product from the alkylation step prior to hydrolysis may be isolated and reacted directly with a compound of the formula IX under similar conditions to those described above to obtain a formula VI compound directly. In a yet further alternative procedure, a 4-methylphenylboronic acid and an appropriate alkanediol, for example 2,2-dimethylpropan-1,3-diol, may be heated at reflux in a solvent (such as cyclohexane) with azeotropic removal of water followed by free radical bromination of the product, which may be carried out in situ. The resultant bromomethyl compound may then be reacted using analogous procedures to those described above for the 4-bromomethylphenylboronic acid anhydride to obtain a formula XIa, XIb, or XIc compound or a compound of the formula VI directly. Compounds of the formula IX may be obtained, for example, as shown in Scheme 1.

Whereafter, when a non-toxic salt of a compound of formula IV is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula IV is required, the aforesaid process may be carried out using an optically active starting material. Alternatively, the racemic form of a compound of formula IV may be resolved, for example by reaction with an optically active form of a suitable organic base, for example, ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula IV may be liberated by treatment with acid using a conventional procedure, for example using an aqueous mineral acid such as dilute hydrochloric acid.

It will be appreciated that an alternative process variant of the present invention involves the use of a starting material of formula VI in which the group $P^1$ is attached to a nitrogen atom of the tetrazole ring other than at the 1-position. The necessary starting materials for such a variant may be made by methods well known in the art for the preparation of structurally analogous compounds.

Certain of the intermediates defined herein are novel, for example the compounds of the formula VI, VIIa, IX and IXa, and are provided as a further feature of the invention, in particular those compounds of formula VI, VIIa, IX and IXa wherein the substituted tetrazolyl group bearing $P^1$ is ortho to the adjacent phenyl group.

The antagonism of one or more of the physiological actions of AII and, in particular, the antagonism of the interaction of AII with the receptors which mediate its effects on a target tissue, may be assessed using one or more of the following, routine laboratory procedures:

Test A: This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}$M are retested at lower concentrations to determine their potency. For determination of the IC$_{50}$ (concentration for 50% displacement of radiolabelled AII binding), concentrations of the test compound are ordinarily chosen to allow testing over at least four orders of magnitude centred about the predicted approximate IC$_{50}$, which latter is subsequently determined from a plot of percentage displacement against concentration of the test compound.

In general, compounds of formula IV wherein Q is a 4-quinolyloxy moiety of the formula Va or a 4-pyridyloxy moiety of the formula Vb as defined above show significant inhibition in Test A at a concentration of 50 micromolar or much less.

Test B: This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, compounds of formula IV wherein Q is a 4-quinolyloxy moiety of the formula Va or a 4-pyridyloxy moiety of the formula Vb as defined above show significant inhibition in Test B at a final concentration of 50 micromolar or much less.

Test C: This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific, the effect of the test compound on vasopressin-induced pressor responses may also be determined in the same preparation.

The compounds of formula IV wherein Q is a 4-quinolyloxy moiety of the formula Va or a 4-pyridyloxy moiety of the formula Vb as defined above generally show specific AII-antagonist properties in Test C at a dose of 50 mg/kg body weight or much less, without any overt toxicological or other untoward pharmacological effect.

Test D: This in vivo test involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula IV wherein Q is a 4-quinolyloxy moiety of the formula Va or a 4-pyridyloxy moiety of the formula Vb as defined above will show AII-antagonist properties in Test D as demonstrated by a significant reduction in blood pressure at a dose of 50 mg/kg body weight or much less, without any overt toxicological or other untoward pharmacological effect.

By way of illustration of the angiotensin II inhibitory properties of compounds of formula IV, 2-methyl-4-[(2'-(1H-tetrazol-5-yl)biphenyl-4-yl)methoxy]quinoline hydrochloride gave the following results in tests A, B and C described above:
In test A: an average IC$_{50}$ of $1.7 \times 10^{-8}$M;
In test B an average pA$_2$ of 8.95;
In test C: ED$_{50}$ of 0.5 mg/kg (i.v. administration).

Similarly, 2-methyl-5,6,7,8-tetrahydro-4-[(2'-(1H-tetrazol-5-yl)methoxy]quinoline hydrochloride gave the following results in test A and C described above:
In test A: IC$_{50}$ of $3 \times 10^{-8}$M;
In test C: ED$_{50}$ of 0.28 mg/kg (i.v. administration).

The invention will now be illustrated by the following non-limiting Examples in which, unless otherwise stated:

(i) concentrations and evaporations were carried out by rotary evaporation in vacuo;

(ii) operations were carried out at room temperature, that is in the range 18°-26° C.;

(iii) yields, where given, are intended for the assistance of the reader only and are not necessarily the maximum attainable by diligent process development;

(iv) $^1$H NMR spectra were normally determined at 270 MHz in CDCl$_3$ using tetramethylsilane (TMS) as an internal standard, and are expressed as chemical shifts (delta values) in parts per million relative to TMS using conventional abbreviations for designation of major peaks: s, singlet; m, multplet; t, triplet; br, broad; d, doublet; and (v) the term "1H-tetrazol-5-yl" stands for "1H-1,2,3,4-tetrazol-5-yl".

EXAMPLE 1

Sodium hydride (50% dispersion in mineral oil; 0.091 g; 1.9 mmol) was washed with hexane, dried with a stream of nitrogen and covered with N-methylpyrrolidone (NMP) (5 ml). The mixture was cooled to below 10° C. and propanethiol (0.145 g; 1.9 mmol) was added slowly with stirring. After 15 minutes, a solution of 2-ethyl-4-[(2'-(1-(4-nitrophenyl)-1H-tetrazol-5-yl)biphenyl-4-yl)methoxy]quinoline (A) (0.5 g; 0.95 mmol) in NMP (10 ml) was added slowly maintaining the temperature of the reaction mixture below 10° C. The mixture was then stirred for 2 hours. Concentrated hydrochloric acid was added until the reaction mixture was pH2. Water (25 ml) was then added and the suspended white solid collected by filtration. The crude product was recrystallised from ethanol to give 2-ethyl-4-[(2'-(1H-tetrazol-5-yl)biphenyl-4-yl)methoxy]quinoline hydrochloride as a solid, in 64% yield; m.p. 178°-181° C.; NMR (d$_6$-DMSO): 1.53(3H, t), 3.30(2H, q), 5.65(2H, s), 7.25(2H, d), 7.50-7.75(6H, m), 7.80(1H, t), 7.90(1H, s), 8.00(1H, t), 8.35(1H, d), 8.50(1H, d).

The starting material A was obtained by procedure A, B or C as follows:

PROCEDURE A (i) Thionyl chloride (120.5 g) was added to a stirred mixture of 2-bromobenzoic acid (194 g) in toluene (500 ml) and N,N-dimethylformamide (DMF) (5 ml) and the mixture heated at 80° C. for 4 hours. The solution was cooled to 20° C. and added slowly to a solution of 4-nitroaniline (133.1 g) in toluene (500 ml) and NMP (120 ml), maintaining the temperature of the reaction mixture between 20°-25° C. The reaction mixture was then stirred for 24 hours when a solid precipitated. Water (360 ml) was added with rigorous stirring and the suspended solid collected by filtration, and washed successively with water, toluene and acetonitrile to give 2-bromo-N-(4-nitrophenyl)benzamide (B) as a solid, in 87% yield; m.p. 200°-202° C.; NMR(d$_6$-DMSO): 7.4-7.8(m, 7H), 8.0(d, 2H), 8.3(d, 2H), 11.5(brs, 1H); which was used without further purification.

(ii) Triethylamine (1.04 g; 10.38 mmol) was added to a mixture of amide B (3 g; 9.35 mmol) in acetonitrile (12 ml) and DMF (0.189 g; 2.58 mmol) and the mixture was stirred for 90 minutes. Thionyl chloride (1.44 g; 12.14 mmol) was then added slowly keeping the reaction temperature below 25° C. The mixture was stirred for 5 hours at ambient temperature and then cooled to 10° C. Triethylamine (2.83 g; 28 mmol) was then added, followed by sodium azide (1.33 g; 20.4 mmol) and tetrabutylammonium bromide (0.42 g; 1.3 mmol). The mixture was stirred for 2 hours at 10° C. and then allowed to warm to ambient temperature and stirred for 24 hours. The mixture was poured into excess water and the precipitated solid collected by filtration. The solid was purified by trituration with a hot mixture of ethyl acetate (26 ml), hexane (2.6 ml) and triethylamine (0.1 ml) to give 5-(2-bromophenyl)-1-(4-nitrophenyl)-1H-tetrazole (C) (2.36 g; 73% yield) as an off-white solid, m.p. 169°–170° C.; NMR ($d_6$-acetone; 270 MHz): 7.61–7.86(m, 6H), 8.41(d, 2H); microanalysis, found: C, 44.8; H, 2.1; N, 20.0; Br, 23.6%; $C_{13}H_8BrN_5O_2$ requires: C, 45.1; H, 2.3; N, 20.2; Br, 23.1%.

(iii) A mixture of 4-methylphenyl boronic acid (9.7 g; 71 mmol), sodium carbonate (16.7 g; 158 mmol), water (100 ml), methanol (50 ml) and toluene (50 ml) was heated to 60° C. to give a clear solution. Compound C (20.0 g; 55 mmol) was then added, followed by tetrakis(triphenylphosphine)palladium (0.3 g; 0.25 mmol) and the mixture heated at reflux for 3 hours. Toluene (30 ml) was added and the warm mixture was filtered through diatomaceous earth. The organic phase was separated and the aqueous phase extracted with toluene (40 ml). The combined organic phases were evaporated to give a solid which was recrystallised from toluene/petroleum ether (100°–120° C.) (1:1 v/v) to give 5-(4'-methylbiphenyl-2-yl)-1-(4-nitrophenyl)-1H-tetrazole (D) (18.7 g; 90% yield), m.p. 164°–166° C.; NMR ($CDCl_3$): 2.3(3H, s), 6.45(2H, d), 6.85(4H, m), 7.38(1H, d), 7.65(2H, m), 7.85(1H, d), 8.0(2H, d).

(iv) A mixture of compound D (8.0 g; 21 mmol), N-bromosuccinimide (4.53 g; 25 mmol) and azo(bisisobutyronitrile) (73 mg) in methyl chloroform (50 ml) was heated at reflux for 4 hours. The mixture was cooled to ambient temperature, washed with water (3×50 ml), and the suspended solid collected by filtration to give 5-(4'-bromomethylbiphenyl-2-yl)-1-(4-nitrophenyl)-1H-tetrazole (E) (7.3 g), m.p. 192°–195° C.; NMR ($\overline{CDCl_3}$): 4.4(2H, s), 6.52(2H, d), 6.85(2H, d), 7.07(2H, d), 7.4(1H, d), 7.7(2H, m), 7.9(1H, d).

(v) A mixture of 2-ethyl-4-quinolone (1.9 g; 11 mmol), (prepared using a similar procedure to that described in *Org. Syn., Coll., Vol.* III, p. 374 and p. 593 from aniline and ethyl propionylacetate), and potassium carbonate (2.28 g; 16 mmol) in NMP (75 ml) was heated at 60° C. for 20 minutes with stirring. Compound E (5.2 g; 10 mmol) was added and the reaction mixture heated at 80° C. for 90 minutes. The mixture was allowed to cool to ambient temperature and water (150 ml) was added. The resultant precipitate was collected by filtration, dried at 60° C., then recrystallised from toluene to give 2-ethyl-4-[(2'-(1-(4-nitrophenyl)-1H-tetrazol-5-yl)biphenyl-4-yl)methoxy]quinoline (A) (1.5 g) as a solid, m.p. 204°–206° C.; NMR ($CDCl_3$): 1.42(3H, t), 3.0(2H, q), 5.23(2H, s), 6.67(2H, d), 6.75(1H, s), 6.85(2H, d), 7.25(2H, d), 7.43(1H, d), 7.55(1H, t), 7.70(3H, m) 7.90(3H, d), 8.05(1H, d), 8.20(1H, d).

PROCEDURE B (i) A mixture of 4-methylphenylboronic acid (27.2 g; 0.2 mole) in methyl chloroform (250 ml) was heated at reflux with azeotropic removal of water until approximately 2.5 ml of water was collected and a crystalline slurry was formed. A solution of azo(bisisobutyronitrile) (1.0 g) and bromine (32 g) in methyl chloroform (25 ml) was added to the refluxing slurry over 2–3 hours. The mixture was then refluxed until the bromine colour was discharged. The reaction mixture was allowed to cool and stirred at 10°–15° C. for 30 minutes. The suspended solid was collected by filtration, washed with methyl chloroform (2×50 ml) and dried at ambient temperature to give the anhydride of 4-bromomethylphenylboronic acid (29 g) (Compound F) as a white, crystalline solid, which was used without further purification or characterisation.

(ii) A mixture of 2-ethyl-4-quinolone (1.0 g), the anhydride of 4-bromomethylphenylboronic acid (compound F), (2.7 g) potassium carbonate (2.0 g) and NMP (5 ml) was heated at 70° C. for 3 hours with stirring. The mixture was allowed to cool and then added slowly to water (50 ml) with vigorous stirring. The mixture was allowed to stand for 20 minutes and then the solid precipitate collected by filtration. The solid was suspended in ethyl acetate (25 ml), concentrated hydrochloric acid (2 ml) was added, and the mixture was then stirred for 30 minutes. Water (10 ml) was added and the mixture allowed to stand for a further 20 minutes. The suspended solid was collected by filtration and washed with ethyl acetate (10 ml) to give 4-[(2-ethylquinolin-4-yloxy)methyl]phenylboronic acid hydrochloride (Compound G) (1.2 g), m.p. 159°–163° C.; NMR ($d_4$-methanol): 1.5(t,3H), 3.21(q,2H), 5.78(s,2H), 7.55(s,1H), 7.6–8.15(m,7H), 8.40(d,2H).

(iii) A mixture of potassium carbonate (5.8 g), 5-(2-bromophenyl)-1-(4-nitrophenyl)-1H-tetrazole (5.81 g) (obtained as described in Procedure A, step (ii)), water (43 ml), toluene (43 ml), and methanol (43 ml) was heated to 60° C. to give a clear solution. 4-[(2-Ethylquinolin-4-yloxy)methyl]phenylboronic acid hydrochloride (4.3 g) and tetrakis(triphenylphosphine)palladium (0.032 g) were added and the reaction mixture heated at reflux for 4 hours. The mixture was allowed to cool and further toluene (50 ml) added. The organic phase was separated and the aqueous phase extracted with toluene (2×50 ml). The combined organic phases were evaported and the resultant solid recrystallised from toluene to give 2-ethyl-4-[(2'-(1-(4-nitrophenyl)-1H-tetrazol-5-yl)biphenyl-4-yl)methoxy]quinoline (A) as a solid (4.3 g); m.p. and NMR similar to that of compound A of Procedure A, part (v).

Alternatively, steps (i) and (ii) of procedure B were replaced by the following procedure:

A solution of 2-ethyl-4-quinolone (6.9 g; 0.04 mole) in (NMP) (50 ml) was added over 30 minutes to a stirred suspension of sodium hydride (1.6 g of a 60% dispersion in mineral oil; 0.04 mole) in NMP (50 ml) and the mixture stirred for 30 minutes. A solution of 2-(4-bromomethylphenyl)-5,5-dimethyl-1,3,2-dioxaborinane in cyclohexane [previously prepared by heating a mixture of 4-methylphenylboronic acid (6.8 g) and 2,2-dimethylpropan-1,3-diol (5.2 g) in cyclohexane (150 ml) at reflux with azeotropic removal of water, followed by the addition of N-bromosuccinimide (8.9 g) and azo(bisisobutyronitrile) (0.2 g), heating the mixture at reflux for 3 hours, and removing suspended succinimide by filtration] was added and the mixture was heated at 60°–70°]C. for 18 hours. The mixture was allowed to cool and acetic acid was then added until the mixture was at pH 4, followed by water (200 ml) and ethyl acetate (200 ml). The mixture was stirred for 20 minutes and then the organic phase was separated, washed with water and dried (MgSO$_4$). Volatile material was removed by evaporation to give a crystalline solid. The solid was dissolved in ethyl acetate (150 ml), concentrated hydrochloric acid (3 ml) and water (3 ml) were added and the mixture was stirred for 18 hours. The resultant precipitate was collected by filtration, washed with ethyl acetate and dried to give 4-[(2-ethylquinolin-4-yloxy)methyl]phenylboronic acid hydrochloride (7 g) as a solid; NMR similar to that of compound G of Procedure B, step (ii).

PROCEDURE C (i) A mixture of 4-methylphenylboronic acid (34.0 g; 0.25 mole) and 2,2-dimethylpropan-1,3-diol 926.0 g; 0.25 mole) was heated in cyclohexane (500 ml) at reflux with azeotropic removal of water. When no further water collected, N-bromosuccinimide (44.5 g) and azo(-bisisobutyronitrile) (1.0 g) was added and the mixture was heated at reflux for 3 hours. Suspended succinimide was removed by filtration and the cooled filtrate was added to a mixture of 2-ethyl-4-quinolone (31.2 g; 0.18 mole), potassium carbonate (38.4 g; 0.21 mole) and NMP (120 ml). The mixture was heated at 60°–70° C. for 18 hours and then allowed to cool. Aqueous potassium carbonate solution (10% w/v; 400 ml) was added and the resulting crystalline precipitate collected by filtration, washed with water and cyclohexane and dried at ambient temperature. There was thus obtained 2-(4-[(2-ethylquinolin-4-yloxy)methyl]phenyl)-5,5-dimethyl-1,3,2-dioxaborinane (H) (37 g), m.p. 154°–156° C.; NMR(CDCl$_3$): 1.03(6H, s), 1.37(3H, t), 2.94(2H, q), 3.80(4H, s), 5.30(2H, s), 6.72(1H, s), 7.4–8.3(8H, m).

(ii) A mixture of potassium carbonate (1.08 g; 7.8 mmol), 5-(2-bromophenyl)-1-(4-nitrophenyl)-1H-tetrazole (1.16 g; 3.2 mmol) (obtained as described in Procedure A, step (ii)), water (10 ml), toluene (10 ml), and methanol (10 ml) was heated to 60° C. to give a clear solution. Compound H (1.0 g; 2.6 mmol) and tetrakis(-triphenylphosphine)palladium (0.06 g; 0.05 mmol) were added and the reaction mixture heated at reflux for 6 hours. The mixture was allowed to cool and further toluene (10 ml) added. The organic phase was separated and the aqueous phase extracted with toluene (2×20 ml). The combined organic phases were evaporated and the resultant solid recrystallised from toluene to give 2-ethyl-4-[(2'-(1-(4-nitrophenyl)-1H-tetrazol-5-yl)biphenyl-4-yl)methoxy]quinoline (A) as a solid (0.8 g); m.p. and NMR similar to that of the product of procedure A, part (v).

EXAMPLE 2

Using an analogous procedure to that described in Example 1, but using ethanol (95%; 0.092 g; 1.9 mmol) in place of propanethiol and stirring the reaction mixture for 4 hours after the addition of compound A, there was thus obtained 2-ethyl-4-[(2'-(1H-tetrazol-5-yl)biphenyl-4-yl)methoxy]quinoline hydrochloride as a solid, in 60% yield; m.p. and NMR similar to that obtained for the product of Example 1.

EXAMPLE 3

Using an analogous procedure to that described in Example 1, but starting from 2-ethyl-4-[(2'-(1-(4-nitrophenyl)-1H-tetrazol-5-yl)biphenyl-4-yl)methoxy]-5,6,7,8-tetrahydroquinoline, there was thus obtained 2-ethyl-5,6,7,8-tetrahydro-4-[(2'-(1H-tetrazol-5-yl)biphenyl-4-yl)methoxy]quinoline hydrochloride as a solid, in 54% yield; m.p. 235°–237° C.; NMR (d6-DMSO): 1.45(3H,t), 1.95(4H,m), 2.75(2H,q), 3.10(4H,m), 5.60(2H,s), 7.32(2H,d), 7.58(3H,m), 7.73(2H,m), 7.85(2H,d).

The starting material was obtained by procedure D or E as follows:

PROCEDURE D

Using an analogous procedure to that described in Procedure A, part (v), but starting from 2-ethyl-5,6,7,8-tetrahydro-4(1H)-quinolone [m.p. 226°–227° C.; NMR (d6-DMSO): 1.15(t,3H), 1.55–1.75(m,4H), 2.25(t,2H), 2.4(q,2H), 2.45–2.55(m,2H), 5.8(s,1H); obtained using an analogous procedure to that described for the preparation of 2-methyl-5,6,7,8-tetrahydro-4(1H)-quinolone in Liebigs Ann. Chem. 1982, 1656 but reducing the intermediate 2-ethyl-4(1H)-quinolone (m.p. 178°–181° C.) by catalytic hydrogenation over platinum oxide in acetic acid at one atmosphere pressure], there was thus obtained 2-ethyl-4-[(2'-(1-(4-nitrophenyl)-1H-tetrazol-5-yl)biphenyl-4-yl)methoxy]-5,6,7,8-tetrahydroquinoline, as a solid in 60% yield; m.p. 205°–207° C.; NMR (CDCl3):1.30(3H,t), 1.90(4H,m), 2.60–3.00(6H,m), 5.04(2H,m), 6.52(2H,d), 6.60(1H,s), 6.80(2H,d), 7.11(2H,d), 7.40(1H,d), 7.67(2H,d), 7.92(3H,m).

PROCEDURE E (i) Sodium hydride (60% dispersion in oil; 180 mg) was added to a mixture of 2-ethyl-5,6,7,8-tetrahydro-4(1H)-quinolone (660 mg) and 4-bromomethylphenylboronic acid (800 mg) (obtained as described in J. Amer. Chem. Soc. 1958, 80, 835) in DMF (12 ml) under an atmosphere of argon. The mixture was stirred for 40 hours and then water (0.2 ml) was added. Volatile material was removed by evaporation and the residue was dissolved in warm 0.5M sodium hydroxide solution (10 ml). Insoluble material was removed by filtration and the filtrate was acidified to pH 4 with 20% citric acid solution. The precipitate solid was collected by filtration, washed with water (20 ml) and dried under high vacuum to give 4-[(2-ethyl-5,6,7,8-tetrahydroquinolin-4-yl)oxymethyl]phenylboronic acid (A) (1.15 g), m.p. 229°–231° C.; NMR (d6-DMSO): 1.3(t,3H), 1.6–1.9(m,4H), 2.5–2.7(m,2H), 2.75–2.95(m,4H), 5.4(s,2H), 7.3(d,2H), 7.4(s,1H, 7.5(d,2H).

(ii) Tetrakis(triphenylphosphine)palladium (40 mg) was added to a suspension of compound A (200 mg) and 5-(2-bromophenyl)-1-(4-nitrophenyl)-1H-tetrazole (202 mg) in toluene (2 ml) ethanol (0.5 ml) and 2M aqueous sodium carbonate (0.58 ml). The mixture was degassed and placed under an atmosphere of argon, then heated under reflux for 12 hours. The resulting solution was cooled to ambient temperature, and dichloromethane (30 ml) and water (10 ml) were added. The organic layer was separated, dried (MgSO$_4$) and the solvent removed by evaporation. The residue was purified by flash chromatography, eluting with ethyl acetate/hexane (3:1 v/v), and the product triturated with ether/hexane to give 2-ethyl-4-[(2'-(1-(4-nitrophenyl)-1H-tetrazol-5-yl)biphenyl-4-yl)methoxy]-5,6,7,8-tetrahydroquinoline (134 mg) as a solid; NMR and m.p. similar to that obtained by procedure D.

EXAMPLE 4

An analogous procedure to that described in Example 1 was used, but 4-fluorothiophenol (0.243 g) was used in place of propanethiol and the reaction mixture was stirred for 16 hours at ambient temperature after the addition of compound A. The reaction mixture was then added to water (10 ml) and washed with ether (2×10 ml). The aqueous phase was adjusted to pH 7 with 1M hydrochloric acid solution, washed with ether (2×10 ml) and acidified to pH 1 with 1M hydrochloric acid solution. The resultant precipitate was collected by filtration and recrystallised from ethanol to give 2-ethyl-4-[(2'-(1H-tetrazol-5-yl)biphenyl-4-yl)methoxy]quinoline hydrochloride as a solid, in 54% yield; m.p. and NMR similar to that obtained for the product of Example 1.

EXAMPLE 5

Using a similar procedure to that described in Example 3, but using sodium methoxide (2 equivalents) or sodium ethoxide (2 equivalents) in NMP in place of sodium hydride and propanethiol and carrying out the reaction at ambient temperature, there was obtained 2-ethyl-5,6,7,8-tetrahydro-4-[(2'-(1H-tetrazol-5-yl)biphenyl-4-yl)methoxy]quinoline hydrochloride in 80-90% yield; m.p. and NMR similar to that obtained for the product of Example 3.

EXAMPLE 6

An analogous procedure to that described in Example 1 was used, but with 2-butyl-4-chloro-5-hydroxymethyl-1-[(2'-(1-(4-nitrophenyl)-1H-tetrazol-5-yl)biphenyl-4-yl)methyl]imidazole in place of compound A and stirring the reaction mixture for 18 hours. The solvent was then removed by evaporation and the residue dissolved in water (5 ml). The aqueous solution was washed with ether (2×10 ml), acidified with 2M hydrochloric acid to pH4 and extracted with dichloromethane (4×15 ml). The combined extracts were washed with saturated sodium chloride solution, dried (MgSO$_4$) and the solvent was removed by evaporation. The residue was then triturated with a mixture of ether and hexane to give 2-butyl-4-chloro-5-hydroxymethyl-1-[(2'-(1H-tetrazol-5-yl)biphenyl-4-yl)methyl]imidazole as a tan solid, in 30% yield; m.p. 102°-105° C.; NMR (CDCl$_3$+d$_6$-DMSO): 0.86(t,3H), 1.34(m,2H), 1.62(m,2H), 2.60(t,2H), 4.47(s,2H), 5.27(s,2H), 7.4-7.75(m,4H), 7.01(d,2H), 7.14(d,2H); mass spectrum (−ve FAB, DMSO/glycerol) 421 (M−H)$^-$.

The starting material 2-butyl-4-chloro-5-hydroxymethyl-1-[(2'-(1-(4-nitrophenyl)-1H-tetrazol-5-yl)biphenyl-4-yl)methyl]imidazole was obtained as follows:

Potassium carbonate (0.48 g) was added to a solution of 2-butyl-4-chloro-5-hydroxymethylimidazole (prepared as described in U.S. Pat. No. 4,355,040) (0.56 g) and 5-(4'-bromomethylbiphenyl-2-yl)-1-(4-nitrophenyl)-1H-tetrazole (1.3 g) in DMF (15 ml) and the mixture was stirred under an atmosphere of argon at 60° C. for 5 hours. The mixture was cooled to ambient temperature, water (60 ml) was added and the mixture was extracted with ethyl acetate (3×50 ml). The combined extracts were washed with satured sodium chloride solution, dried (MgSO$_4$) and the solvent removed by evaporation. The residue was purified by flash chromatography, eluting with ethyl acetate/hexane (1:1 v/v), to give 2-butyl-4-chloro-5-hydroxymethyl-1-[(2'-(1-(4-nitrophenyl)-1H-tetrazol-5-yl)biphenyl-4-yl)methyl]imidazole (180 mg) as a pale yellow solid, m.p. 182°-186° C.; NMR (CDCl$_3$) 0.87(t,3H), 1.32(m,2H), 1.65(m,2H), 2.49(t,2H), 4.57(s,2H), 5.15(s,2H), 6.58(d,2H), 6.75(d,2H), 6.90(dd,2H), 7.36(dd,1H), 7.65(m,2H), 7.85(dd,1H), 8.00(dd,2H); mass spectrum (+ve FAB, DMSO/CH$_3$OH/m-nitrobenzyl alcohol): 544 (M+H)$^+$.

EXAMPLE 7

Sodium methoxide (30 wt % solution in methanol; 7.2 ml) was added to a solution of 2-ethyl-4-[(2'-(1-(4-nitrophenyl)-1H-tetrazol-5-yl)biphenyl-4-yl)methoxy]quinoline (10 g) in NMP (30 ml) at 15°-20° C. and the solution was stirred for 4 hours. Methyl isobutyl ketone (30 ml) was added and the mixture was heated to 40° C. Concentrated hydrochloric acid (5.8 ml) was added dropwise maintaining the temperature at 40°-45° C. Water (60 ml) was then added and the mixture was stirred for 15 minutes at 40° C. The mixture was cooled to ambient temperature and the suspended solid collected by filtration. The solid was washed with water (2×8 ml), followed by ethanol (2×8 ml), and then dried under vacuum at 30° C. There was thus obtained 2-ethyl-4-[(2'-(1H-tetrazol-5-yl)biphenyl-4-yl)methoxy]quinoline hydrochloride as a solid*, in 74% yield.

[*Recrystallisation from ethanol gives a product with m.p. and NMR similar to that obtained for the product of Example 1].

EXAMPLES 8-12

A similar procedure to that described in Example 7 was carried out separately with each of the following starting materials of formula VI to give 2-ethyl-4-[(2'-(1H)-tetrazol-5-yl)biphenyl-4-yl)methoxy]quinoline hydrochloride in yields of 5 to 40%:

2-ethyl-4-[(2'-(1-(4-N,N-dimethylsulphonamidophenyl)-1H-tetrazol-5-yl)biphenyl-4-yl)methoxy)quinoline (used in Example 8); m.p. 70°-80° C.;

2-ethyl-4-[(2'-(1-(4-cyanophenyl)-1H-tetrazol-5-yl)biphenyl-4-yl)methoxy]quinoline (used in Example 9); m.p. 224°-5° C.;

2-ethyl-4-[2'-(1-(4-cyano-3-trifluoromethylphenyl)-1H-tetrazol-5-yl)-biphenyl-4-yl)methoxy]quinoline (used in Example 10); m.p. 165°-6° C.;

2-ethyl-4-[(2'-(1-(4-methylsulphonylphenyl)-1H-tetrazol-5-yl)biphenyl-4-yl)methoxy]quinoline (used in Example 11); m.p. 211°-3° C.;

2-ethyl-4-[(2'-(1-(4-pyridyl)-1H-tetrazol-5-yl)biphenyl-4-yl)methoxy]quinoline (used in Example 12); m.p. 155°-170° C.

The starting materials of formula VI used in Examples 8 and 9 were obtained using an analogous procedure to that described in Procedure A, steps (i) to (v) of Example 1, starting from 4-(N,N-dimethylsulphonamido)aniline and 4-cyanoaniline respectively. The intermediates thus obtained were as follows:

2-bromo-N-(4-N,N-dimethylsulphonamido)benzamide, m.p. 184°-6° C.;

2-bromo-N-(4-cyanophenyl)benzamide; m.p. 187° C.;

5-(2-bromophenyl)-1-(4-(N,N-dimethylsulphonamido)-phenyl-1H-tetrazole; m.p. 169°-170° C.;

5-(2-bromophenyl)-1-(4-cyanophenyl)-1H-tetrazole; m.p. 117°-8° C.;

5-(4'-methylbiphenyl-2-yl)-1-(4-(N,N-dimethylsulphonamido)phenyl-1H-tetrazole; m.p. 182°-4° C.;

5-(4'-methylbiphenyl-2-yl)-1-(4-cyanophenyl)-1H-tetrazole; NMR (CDCl$_3$): 2.3(s, 3H), 6.4–7.9(m, 12H);

5-(4'-bromomethylbiphenyl-2-yl)-1-(4-(N,N-dimethylsulphonamido)phenyl-1H-tetrazole; m.p. 174°–6° C.;

5-(4'-bromomethylbiphenyl-2-yl)-1-(4-cyanophenyl)-1H-tetrazole; m.p. 198°–200° C.

The starting material of formula VI used in Example 10 was obtained using a analogous procedure to that described in Procedure C of Example 1, but using 5-(2-bromophenyl)-1-(4-cyano-3-trifluoromethylphenyl)-1H-tetrazole in step (ii), itself obtained using a similar procedure to that described in Procedure A, steps (i) and (ii) of Example 1, starting from 4-cyano-3-trifluoromethylaniline (obtained as described in J. Am. Chem. Soc., 1954, 76, 1051).

The intermediates thus obtained were as follows:

2-bromo-N-(4-cyano-3-trifluoromethylphenyl)benzamide; m.p. 156°–160° C.; 5-(2-bromophenyl)-1-(4-cyano-3-trifluoromethylphenyl)-1H-tetrazole; m.p. 177°–9° C.

The starting material of formula VI used in Example 11 was obtained using a similar procedure to that described in Procedure A, steps (ii) to (v) of Example 1, starting from 2-bromo-N-(4-methylsulphonylphenyl)benzamide. The intermediates thus obtained were as follows:

5-(2-bromophenyl)-1-(4-methylsulphonylphenyl(-1H-tetrazole; m.p. 172°–5° C.;

5-(4'-methylbiphenyl-2-yl)-1-(4-methylsulphonylphenyl)-1H-tetrazole; NMR (CDCl$_3$): 2.4(s, 3H), 3.4(s, 3H), 6.5–8.1(m, 12H); and 5-(4'-bromomethylbiphenyl-2-yl)-1-(4-methylsulphonylphenyl)-1H-tetrazole; m.p. 192°–4° C.

2-bromo-N-(4-methylsulphonylphenyl)benzamide was obtained as follows:

(i) 2-Bromobenzoic acid (40 g), acetonitrile (100 ml) and thionyl chloride (16 ml) was heated together at reflux for one hour. The solution was cooled to ambient temperature and added to a slurry of 4-methylmercaptoaniline hydrochloride (8.7 g) in acetonitrile (100 ml). The mixture was cooled to below 5° C. and triethylamine (17.3 ml) was added. The mixture was then allowed to warm to ambient temperature and water (50 ml) was added. The precipitated solid was collected by filtration and washed sequentially with 4% aqueous sodium hydroxide solution (2×25 ml), 4% hydrochloric acid solution (2×25 ml) and water (50 ml). The solid was dried under vacuum to give 2-bromo-N-(4-methylmercaptophenyl)benzamide (A) (13.5 g); m.p. 137°–8° C.

(ii) The benzamide A (3.2 g), toluene (20 ml) and formic acid (5 ml) were heated at 60° C. and a solution of hydrogen peroxide in water (60% w/v; 1.2 ml) was added slowly. The mixture was stirred for 45 minutes and then a further 1.2 ml of the aqueous hydrogen peroxide solution was added. The mixture was heated at 60°–70° C. for 3 hours and then cooled. The solid which crystallised was collected by filtration and washed with 2M sodium thiosulphate solution (10 ml), water (10 ml) and toluene (2×10 ml). The solid was dried under vacuum to give 2-bromo-N-(4-methylsulphonylphenyl)benzamide (3 g), m.p. 168°–9° C.

The starting material of formula VI used in Example 12 was obtained using a similar procedure to that described in Procedure B, step (iii) of Example 1, but starting from 5-(2-bromophenyl)-1-(4-pyridyl)-1H-tetrazole (and using palladium(II) chloride in place of tetrakis(triphenylphosphine)palladium), itself obtained using an analogous procedure to that described in Procedure A, steps (i) and (ii) of Example 1, starting from 4-aminopyridine. The intermediates thus obtained were as follows:

2-bromo-N-(4-pyridyl)benzamide; m.p. 185°–6° C.; and 5-(2-bromophenyl)-1-(4-pyridyl)-1H-tetrazole; m.p. 121°–2° C.

EXAMPLE 13

Using a analogous procedure to that described in Example 7 but starting from 2-ethyl-4-[(2'-(1-(4-nitrophenyl)-1H-tetrazol-5-yl-biphenyl-4-yl)methoxy]-5,6,7,8-tetrahydroquinoline, there was thus obtained 2-ethyl-5,6,7,8-tetrahydro-4[(2'-(1H-tetrazol-5-yl)biphenyl-4-yl)methoxy]quinoline hydrochloride in 70% yield, m.p. and NMR similar to that obtained for the product of Example 3.

Chemical Formulae

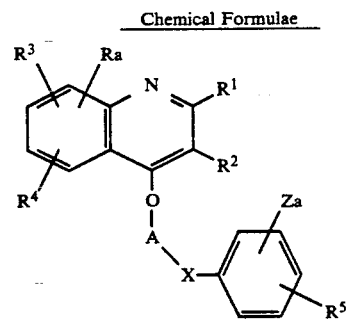

I

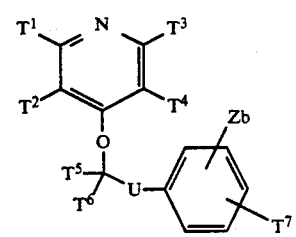

II

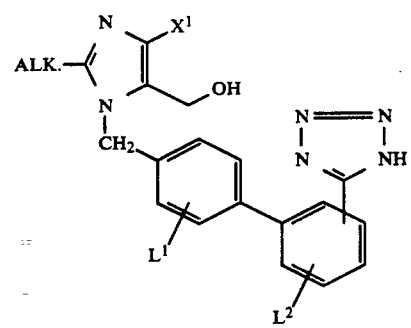

III

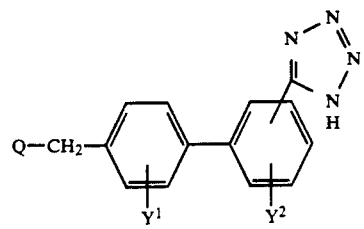

IV

-continued
Chemical Formulae
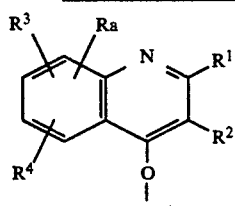 Va
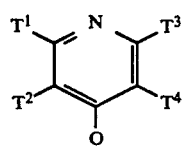 Vb
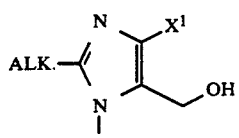 Vc
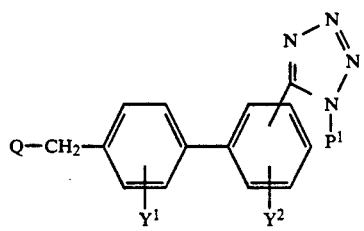 VI
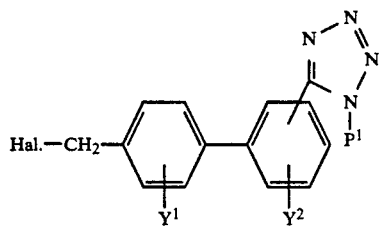 VIIa
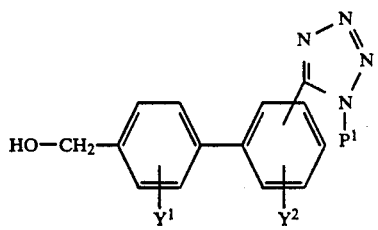 VIIb
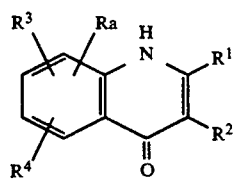 VIIIa
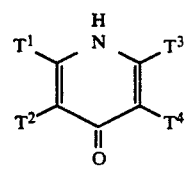 VIIIb
-continued
Chemical Formulae
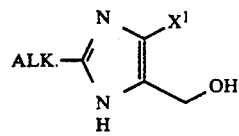 VIIIc
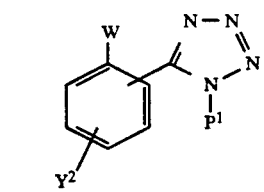 IX
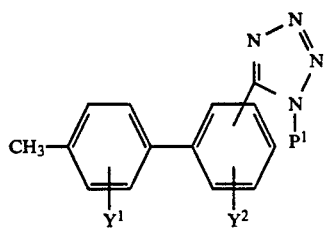 IXa
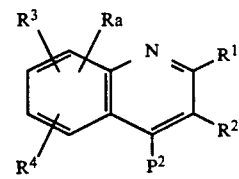 Xa
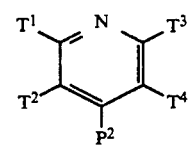 Xb
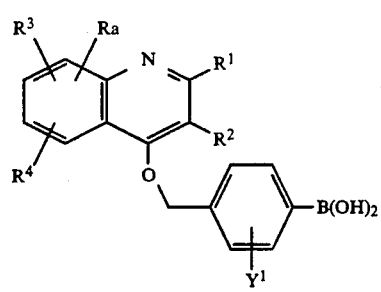 XIa
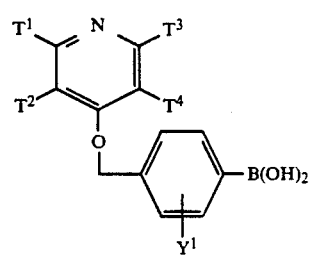 XIb -continued
Chemical Formulae

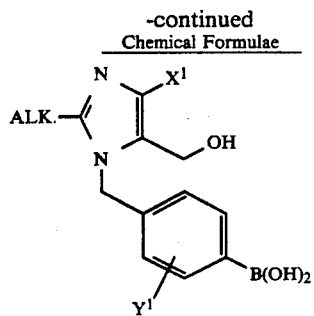

XIc

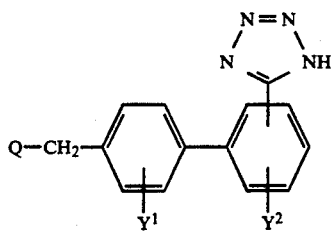

IV or a non-toxic salt thereof, wherein Q is selected from
(1) a 4-quinolyloxy moiety of the formula Va Scheme 1

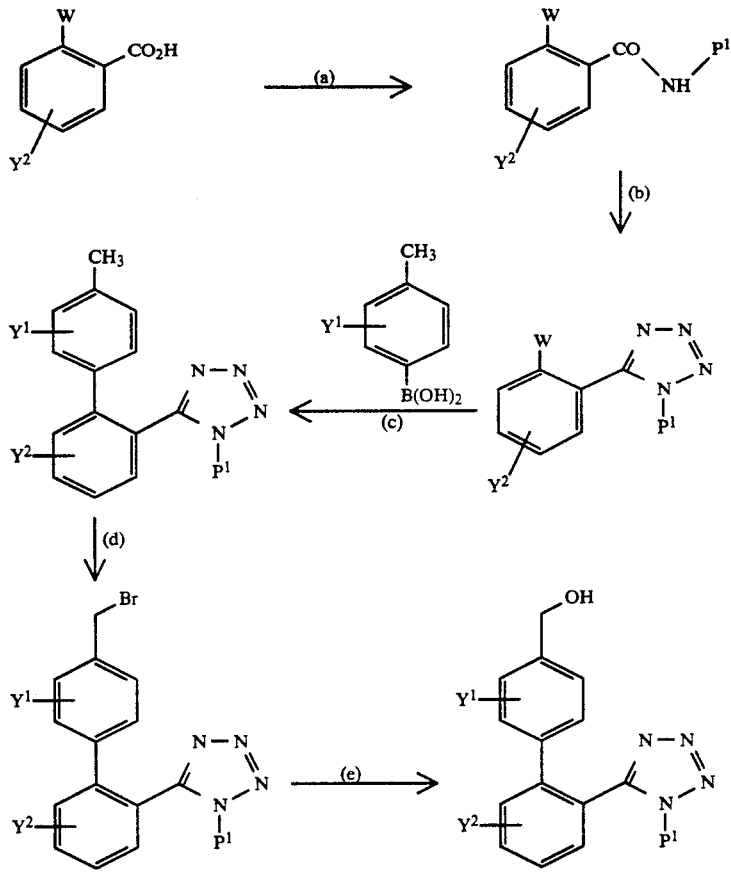

Reagents:
(a) SOCl₂, DMF, toluene, 80° C.; then add to P¹.NH₂, toluene, NMP, ambient temperature
(b) (i) Et₃N, CH₃CN, DMF; (ii) SOCl₂, 10° C.; and (iii) Et₃N, NaN₃, tetrabutylammonium bromide, 10° C. to ambient
(c) Add product of (b) and (Ph₃P)₄Pd to pre-formed solution of (4-CH₃)(Y¹)C₆H₄.B(OH)₂, Na₂CO₃, H₂O, MeOH, toluene, 60° C.; then reflux
(d) NBS, azo(bisisobutyronitrile), CH₃CCl₃
(e) (i) Potassium acetate, hexaoxacyclooctadecane, dimethoxyethane, reflux (ii) LiBH₄, THF, 0–25° C.

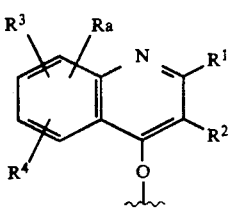

Va

What we claim is:
1. A process for the manufacture of a compound of the formula IV in which $R^1$ is hydrogen, (1–8C)alkyl, (3–8C)cycloalkyl, phenyl or substituted (1–4C)alkyl, the latter containing one or more fluoro substituents or bearing a (3–8C)cycloalkyl, hydroxy, (1–4C)alkoxy or phenyl substituent; R² is hydrogen, (1–8C)alkyl, (3–8C)cycloalkyl, (3–8C)cycloalkyl-(1–4C)alkyl, carboxy, (1–4C)alkoxycarbonyl, cyano, nitro, phenyl or phenyl(1–4C)alkyl; R³ and R⁴ are independently selected from hydrogen, (1–4C)alkyl, (1–4C)alkoxy, fluoro(1–4C)alkoxy, halogeno, hydroxy, trifluoromethyl, cyano, nitro, amino, (1–4C)alkanoylamino, alkylamino and dialkylamino of up to 6 carbon atoms, dialkylamino-alkyl of 3 to 8 carbon atoms, (1–4C)alkanoyl, carbamoyl, N-alkylcarbamoyl and di-(N-alkyl)carbamoyl of up to 7 carbon atoms, carboxy, (1–4C)alkoxycarbonyl, (1–6C)alkylthio, (1–6C)alkylsulphinyl, (1–6C)alkylsulphonyl, and substituted (1–4C)alkyl, the latter bearing an amino, hydroxy or (1–4C)alkoxy substituent; or R³ and R⁴ together form (1–4C)alkylenedioxy attached to adjacent carbon atoms of the benzene moiety of formula I; and Ra is selected from hydrogen, (1–4C)alkyl, (1–4C)alkoxy, halogeno, trifluoromethyl, cyano or nitro;

(2) a 4-pyridyloxy moiety of the formula Vb

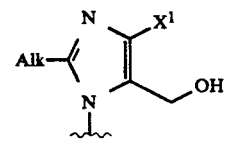

in which T¹ is hydrogen, (1–8C)alkyl, (3–8C)cycloalkyl, phenyl or substituted (1–4C)alkyl, the latter containing one or more fluoro substituents or bearing a (3–8C)cycloalkyl, (1–4C)alkoxy or phenyl substituent; T² is hydrogen, (1–8C)alkyl, (3–8C)cycloalkyl, (3–8C)cycloalkyl-(1–4C)alkyl, carboxy, (1–4C)alkoxycarbonyl, (3–6C)alkenyloxycarbonyl, cyano, nitro, phenyl or phenyl(1–4C)alkyl; T³ is selected from halogeno, (1–4C)alkoxy, amino, alkylamino and dialkylamino of up to 6 carbon atoms, and any of the values defined above for T¹; T⁴ is selected from hydrogen, (1–4C)alkyl optionally bearing an amino, (1–4C)alkanoylamino, phenylcarbonylamino, hydroxy or (1–4C)alkoxy substituent, carboxy, (1–4C)alkoxycarbonyl, (3–6C)alkenyloxycarbonyl, cyano, nitro, carbamoyl, (1–4C)alkanoyl, N-alkylcarbamoyl and di-(N-alkyl)carbamoyl of up to 7 carbon atoms, formyl, halogeno, amino, alkylamino and dialkylamino of up to 6 carbon atoms, 3-(1–4C)alkylureido and (1–4C)alkanoylamino; or T⁴ is a group of the formula —A¹.A².E wherein A¹ is carbonyloxy, A² is (1–6C)alkylene and E is selected from hydroxy, (1–4C)alkoxy, phenyloxy, phenyl(1–4C)alkoxy, pyridyl(1–4C)alkoxy, 4-morpholino(1–4C)alkoxy, phenylamino, amino, alkylamino and dialkylamino of up to 6 carbon atoms, (1–4C)alkanoylamino, (1–4C)alkylsulphonylamino, phenylsulphonylamino, sulphamoylamino (—NH.SO₂.NH₂), carboxamidomethylamino (—NH.CH₂.CO.NH₂), (1–4C)alkanoyloxy, phenylcarbonyloxy, aminocarbonyloxy (—O.CO.NH₂), (1–4C)alkylaminocarbonyloxy, carboxy, (1–4C)alkoxycarbonyl, carbamoyl, N-alkylcarbamoyl and di-(N-alkyl)carbamoyl of up to 7 carbon atoms, (1–4C)alkanoyl, 4-morpholino, 1-imidazolyl and succinimido group; or E is a group of the formula —A³.E¹ wherein A³ is oxy, oxycarbonyl or imino and E¹ is a 5 or 6-membered saturated or unsaturated heterocyclic ring containing 1 or 2 nitrogen atoms and linked to A³ by a ring carbon atom; or A³ is oxycarbonyl and E¹ is a 4-morpholino group or a 5 or 6-membered saturated heterocyclic ring containing 1 or 2 nitrogen atoms, optionally bearing a (1–4C)alkyl group and linked to A³ by a ring nitrogen atom; and wherein E¹ the remainder of the ring atoms are carbon; or T³ and T⁴ together form (3–6C)alkylene, one of the methylene groups of which may optionally be replaced by a carbonyl group, or (3–6C)alkenylene; and (3) an 1-imidazolyl moiety of the formula Vc

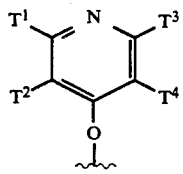

in which Alk. is a (3–10C)alkyl group and X¹ is selected from hydrogen, fluoro, chloro, bromo, iodo, nitro, trifluoromethyl and cyano;

Y¹ is selected from hydrogen, 91–4C)alkyl, (1–4C)alkoxy, halogeno, (1–4C)alkanoyl, trifluoromethyl, cyano and nitro; and Y² is selected from hydrogen, (1–4C)alkyl, (1–4C)alkoxy, halogeno, trifluoromethyl, cyano and nitro;

which is characterised in that a compound of the formula VI

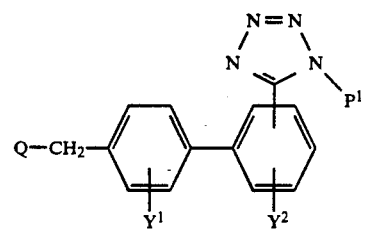

wherein P¹ is an electron-deficient phenyl group or is a pyridyl or pyrimidyl group, and Q, Y¹ and Y² have any of the meanings defined hereinbefore, is reacted with a base selected from an alkali metal hydroxide, (1–12C)alkanolate, (1–12C)alkanethiolate, phenolate, thiophenolate and diphenylphosphide, wherein any phenyl ring of the latter three groups may optionally bear a (1–4C)alkyl, (1–4C)alkoxy or halogeno substituent;

whereafter: when a non-toxic salt of a compound of formula IV is desired, it is obtained by reaction with the appropriate acid or base affording a physiologically acceptable ion, or by any other conventional salt formation procedure; and when an optically active form of a compound of formula IV is desired the process is carried out with an optically active starting material, or a racemic form of a compound of formula IV is resolved by reaction with an optically active form of a suitable organic base followed by conventional separation of the diastereomeric mixture of salts thus obtained, and liberation of the desired optically active form of said compound of formula IV by conventional treatment with acid; and wherein Q, $Y^1$ and $Y^2$ have any of the meanings defined above.

2. A process as claimed in claim 1 wherein, in the starting material of formula VI, $P^1$ is an electron-deficient phenyl group and $Y^1$ and $Y^2$ are independently selected from hydrogen, (1–4C)alkyl, (1–4C)alkoxy, halogeno, trifluoromethyl, cyano and nitro.

3. A process as claimed in claim 1 wherein, in the starting material of formula VI, Q is selected from
2-methyl-4-quinolyloxy,
2-ethyl-4-quinolyloxy,
2-ethyl-7-hydroxymethyl-4-quinolyloxy,
2-ethyl-6-(2-fluoroethoxy)-4-quinolyloxy;
2-ethyl-6-(2,2,2-trifluoroethoxy)-4-quinolyloxy;
2-ethyl-6-isopropoxy-4-quinolyloxy;
2,6-dimethyl-3-(methoxycarbonyl)-4-pyridyloxy,
2-ethyl-5,6,7,8-tetrahydro-4-quinolyloxy,
6,7-dihydro-2-methyl-5H-cyclopenta[b]pyrid-4-yloxy,
2-ethyl-6-methyl-3-(methoxycarbonyl)-4-pyridyloxy,
6-ethyl-2-methyl-3-(methoxycarbonyl)-4-pyridyloxy,
2,6-dimethyl-3-(methoxycarbonyl)-4-pyridyloxy,
6,7-dihydro-2-ethyl-5H-cyclopenta[b]pyrid-4-yloxy,
2,6-dimethyl-3-phenyl-4-pyridyloxy,
2,6-dimethyl-3-(allyloxycarbonyl)-4-pyridyloxy and
2-butyl-4-chloro-5-(hydroxymethyl)-1-imidazolyl;
$Y^1$ and $Y^2$ are both hydrogen; and the tetrazole group is attached at the ortho position relative to the adjacent phenyl group.

4. A process as claimed in claim 1 wherein, in the starting material of formula VI, Q is 2-ethyl-4-quinolyloxy.

5. A process as claimed in claim 1 wherein, in the starting material of formula VI, Q is 2-ethyl-5,6,7,8-tetrahydro-4-quinolyloxy.

6. A process as claimed in claim 1 wherein, in the starting material of formula VI, $P^1$ is a pyridyl group, a pyrimidyl group, or a phenyl group bearing 1, 2 or 3 electron-withdrawing groups independently selected from halogeno, nitro, cyano, trifluoromethyl, di(1–4C)alkylaminosulphonyl and (1–4C)alkylsulphonyl.

7. A process as claimed in claim 1 wherein, in the starting material of formula VI, $P^1$ is 4-nitrophenyl.

8. A process as claimed in claim 1 wherein the starting material of formula VI is reacted with a base selected from sodium hydroxide, potassium hydroxide, sodium methoxide, potassium methoxide, sodium ethoxide, potassium propoxide, sodium butoxide, potassium butoxide, sodium methanethiolate, potassium methanethiolate, sodium ethanethiolate, potassium ethanethiolate, sodium propanethiolate, potassium propanethiolate, sodium butanethiolate, potassium butanethiolate, sodium phenolate and potassium phenolate, sodium thiophenolate and potassium thiophenolate, the phenyl ring of which last four bases being unsubstituted or bearing a methyl, ethyl, methoxy, ethoxy, fluoro, chloro, bromo or iodo group.

9. A process as claimed in claim 1 wherein the starting material of formula VI is reacted with a base selected from sodium methoxide, potassium methoxide, sodium ethoxide and potassium ethoxide.

* * * * *

UNITED STATES PATENT AND TRADEMARK OFFICE
CERTIFICATE OF CORRECTION

PATENT NO. : 5,294,716

DATED : MARCH 15, 1994

INVENTOR(S) : THOMAS ET AL.

It is certified that error appears in the above-identified patent and that said Letters Patent is hereby corrected as shown below:

Column 24, line 27, "$Y^1$ is selected from hydrogen, 91-4C)alkyl," should read --$Y^1$ is selected from hydrogen, (1-4C)alkyl,--.

Signed and Sealed this

Twenty-fifth Day of February, 1997

Attest:

BRUCE LEHMAN

Attesting Officer

Commissioner of Patents and Trademarks